United States Patent
Hokamura et al.

(10) Patent No.: US 8,531,669 B2
(45) Date of Patent: Sep. 10, 2013

(54) AIR-DRIVEN SHUTTER DEVICE AND OPTICAL ANALYZER

(75) Inventors: Shigeyuki Hokamura, Kyoto (JP); Toshikazu Ohnishi, Kyoto (JP); Takuya Ido, Kyoto (JP)

(73) Assignee: Horiba, Ltd., Kyoto (JP)

( * ) Notice: Subject to any disclaimer, the term of this patent is extended or adjusted under 35 U.S.C. 154(b) by 88 days.

(21) Appl. No.: 13/198,017

(22) Filed: Aug. 4, 2011

(65) Prior Publication Data

US 2012/0033218 A1    Feb. 9, 2012

(30) Foreign Application Priority Data

Aug. 4, 2010  (JP) ................... 2010-175734

(51) Int. Cl.
*G01N 21/84*    (2006.01)
(52) U.S. Cl.
CPC .................... *G01N 21/84* (2013.01)
USPC ......................... 356/432; 356/437
(58) Field of Classification Search
CPC .................................................. G01N 21/84
USPC ............... 356/432–444, 334–343
See application file for complete search history.

(56) References Cited

U.S. PATENT DOCUMENTS

| | | | |
|---|---|---|---|
| 3,958,592 A | 5/1976 | Wells et al. | |
| 5,242,224 A * | 9/1993 | Yoshioka et al. | 374/153 |
| 6,152,167 A | 11/2000 | Baker | |
| 7,469,717 B2 | 12/2008 | Leadley | |
| 2004/0179187 A1 | 9/2004 | Mettes | |
| 2006/0176484 A1* | 8/2006 | Steenhoek et al. | 356/413 |

FOREIGN PATENT DOCUMENTS

| | | |
|---|---|---|
| DE | 10003072 A1 | 8/2000 |
| WO | 03096497 A1 | 11/2003 |
| WO | 2004032177 A2 | 4/2004 |

OTHER PUBLICATIONS

Partial European Search Report for EP 11006388, Completed by the European Patent Office on Nov. 2, 2011, 6 Pages.
European Extended Patent Search, issued Feb. 17, 2012.

* cited by examiner

*Primary Examiner* — Michael P Stafira
(74) *Attorney, Agent, or Firm* — Brooks Kushman P.C.

(57) ABSTRACT

An air-driven shutter device is used in an optical analyzer. The optical analyzer includes a measurement field to which a sample is supplied, a light-emitting unit measurement field for emitting measuring light to the sample, a light-receptive unit for receiving the measuring light that has passed through the sample, and a purge air supplying unit for supplying purge air. The air-driven shutter device includes a shutter and a shutter opening and closing mechanism. The shutter is disposed between the light-emitting unit and/or the light-receptive unit and the measurement field. The shutter opening and closing mechanism keeps the shutter open with pressure of the gas supplied from the purge air supplying unit, and closes the shutter when the pressure of the gas supplied from the purge air supplying unit becomes lower than a predetermined level.

11 Claims, 10 Drawing Sheets

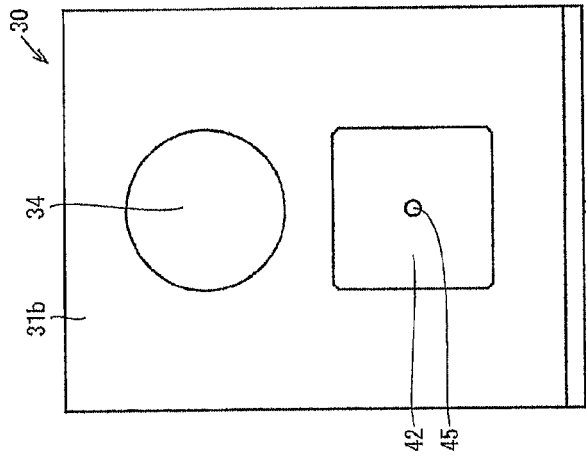
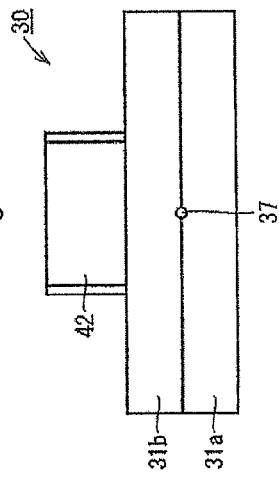
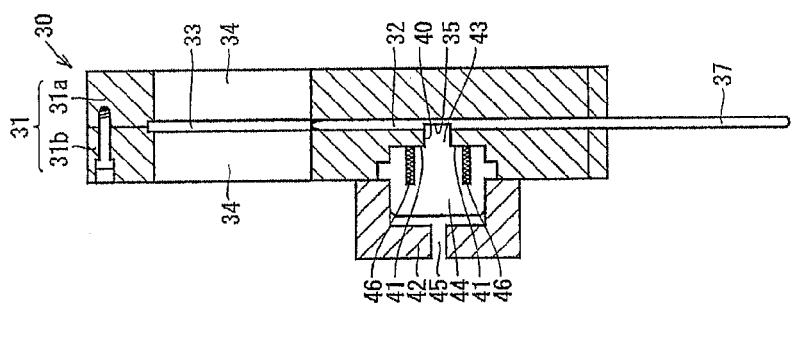
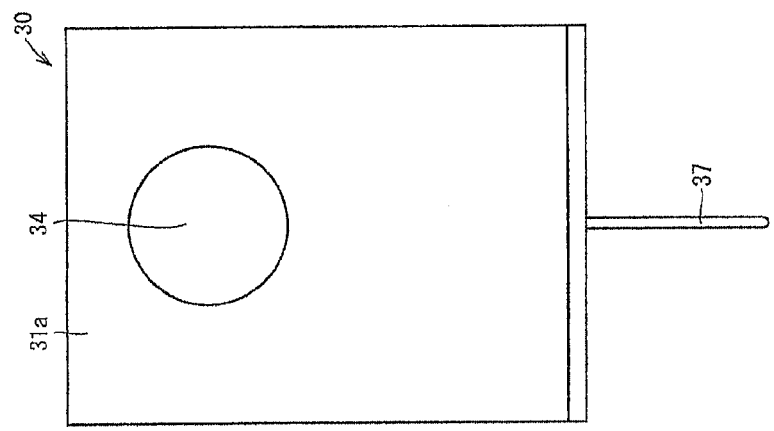
FIG. 3C
FIG. 3D
FIG. 3B
FIG. 3A

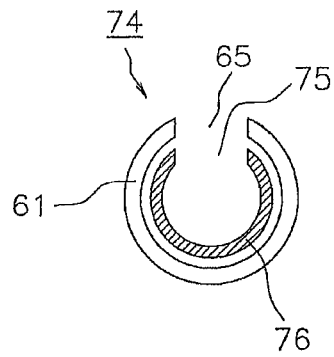 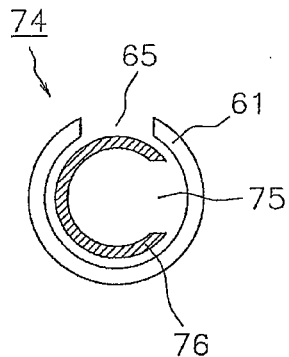
FIG. 10A                FIG. 10B
FIG. 11A
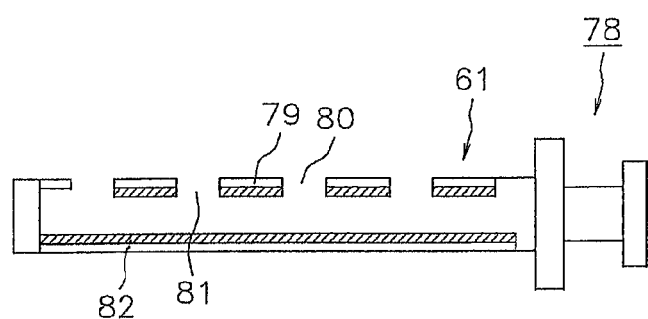
FIG. 11B
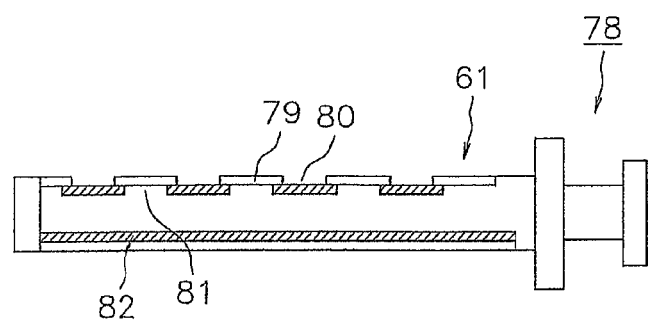

AIR-DRIVEN SHUTTER DEVICE AND OPTICAL ANALYZER

CROSS-REFERENCE TO RELATED APPLICATIONS

This application claims priority under 35 U.S.C. §119 to Japanese Patent Application No. 2010-175734 filed on Aug. 4, 2010. The entire disclosure of Japanese Patent Application No. 2010-175734 is hereby incorporated herein by reference.

BACKGROUND

1. Technical Field

The present disclosure is related to air-driven shutter devices and optical analyzers.

2. Background Information

Conventionally, in optical analyzers, a fail-safe mechanism is provided to reduce or eliminate damage from anomalous operation. Such a device is disclosed in the specification of U.S. Pat. No. 7,469,717, which provides a fail-safe shutter. The fail-safe shutter includes a gate that slides over a round hole to cover or close the hole. The gate is urged by a spring to close the hole, and a clutch is connected to the gate to transmit the power from a motor. Accordingly, when power is supplied to the motor, the hole is opened. In contrast, when the power fails to be supplied, the clutch is disengaged, and the gate is urged by the spring so that the hole is covered.

In the prior art fail-safe shutter described above, the electric power always has to be supplied to the motor, and a control circuit is provided for controlling the electric power. That is, the configuration of the fail-safe shutter becomes complicated, and it is necessary to provide the motor and the control circuit, which results in the shutter being expensive. In addition, the constant electric power supply is not preferable in light of energy conservation.

SUMMARY

Embodiments according to the present disclosure were conceived to solve the above-described problems by providing an air-driven shutter device and an optical analyzer with the air-driven shutter device, in which the electric power is unnecessary and a simple configuration and reasonable cost is realized.

According to a first aspect of the present disclosure, an air-driven shutter device is disclosed, which may be used in, or with, an optical analyzer. The optical analyzer includes a measurement field into which a sample is supplied, a light-emitting unit for emitting measuring light to the sample in the measurement field, a light-receptive unit for receiving the measuring light that passed through the sample, and a purge air supplying unit for supplying purge air. The air-driven shutter device includes a shutter provided between the measurement field and at least one of the light-emitting unit and the light-receptive unit, and a shutter opening and closing mechanism. The mechanism operates such that the shutter is open due to pressure of the gas supplied by the purge air supplying unit, and is closed when the pressure of the gas from the purge air supplying unit becomes lower than a predetermined level.

In one embodiment, a method of operating an optical analyzer including a measurement field to which a sample is supplied, a light-emitting unit configured to emit measuring light to the sample in the measurement field, and a light-receptive unit configured to receive the measuring light that has passed through the sample, includes opening a shutter disposed between the measurement field and at least one of the light-emitting unit and the light-receptive unit using gas pressure and closing the shutter when the gas pressure becomes lower than an associated threshold. The gas pressure may be supplied by a purge air supplying unit, for example.

These and other objects, features, aspects and advantages of the present invention will become apparent to those skilled in the art from the following detailed description, which, taken in conjunction with the annexed drawings, discloses preferred embodiments according to the present disclosure.

BRIEF DESCRIPTION OF THE DRAWINGS

FIG. 3A is a front view of an air-driven shutter device shown in FIG. 1, FIG. 3B is a right side cross-sectional view of the device, FIG. 3C is a rear view of the device, and FIG. 3D is a bottom view of the device;

FIG. 10A and FIG. 10B are longitudinal sectional views of a probe for gas analysis according to another embodiment.

FIG. 11A and FIG. 11B are longitudinal sectional views of a probe for gas analysis according to another embodiment.

DETAILED DESCRIPTION

Selected embodiments of the present disclosure will now be explained with reference to the drawings. It will be apparent to those skilled in the art from this disclosure that the following descriptions of the embodiments are provided as examples only and are not meant to limit the invention defined by the appended claims and their equivalents. Various features illustrated and/or described with respect to a particular embodiment may be combined with features illustrated and/or described with respect to one or more other embodiments to produce embodiments of the present disclosure that may not be explicitly illustrated or described. The combinations of features explicitly illustrated and/or described provide representative embodiments for typical applications. However, various combinations and modifications of the features consistent with the teachings of the present disclosure may be desired for particular applications or implementations.

1. First Embodiment

1-1. Air-Driven Shutter Device

Hereinafter, an embodiment according to the present disclosure will be explained with reference to the drawings.

An air-driven shutter device according to the present embodiment is provided in a path which connects a gas cell, through which sample gas passes, to a light-emitting unit and a light-receptive unit of the optical analyzer (e.g., an infrared gas analyzing apparatus). Here, first of all, an overall operation of the air-driven shutter device will be explained.

Figure 1A:
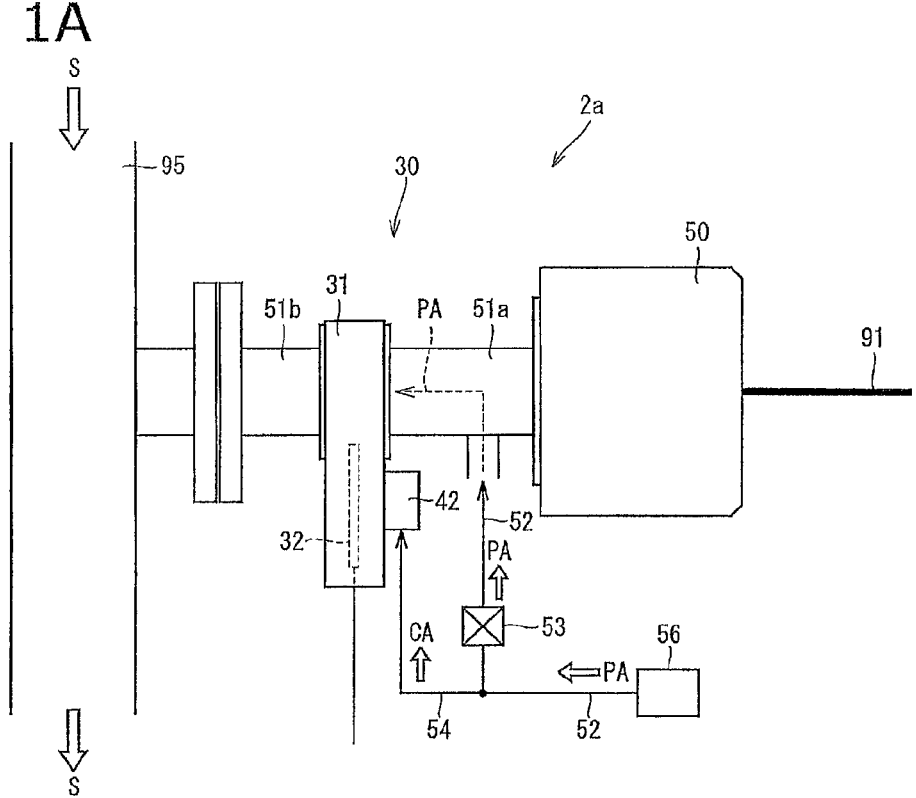
FIG. 1A and FIG. 1B are side views illustrating a light-emitting unit of an optical analyzer and its surroundings, including an air-driven shutter device according to one embodiment of the present disclosure.
Figure 1B:
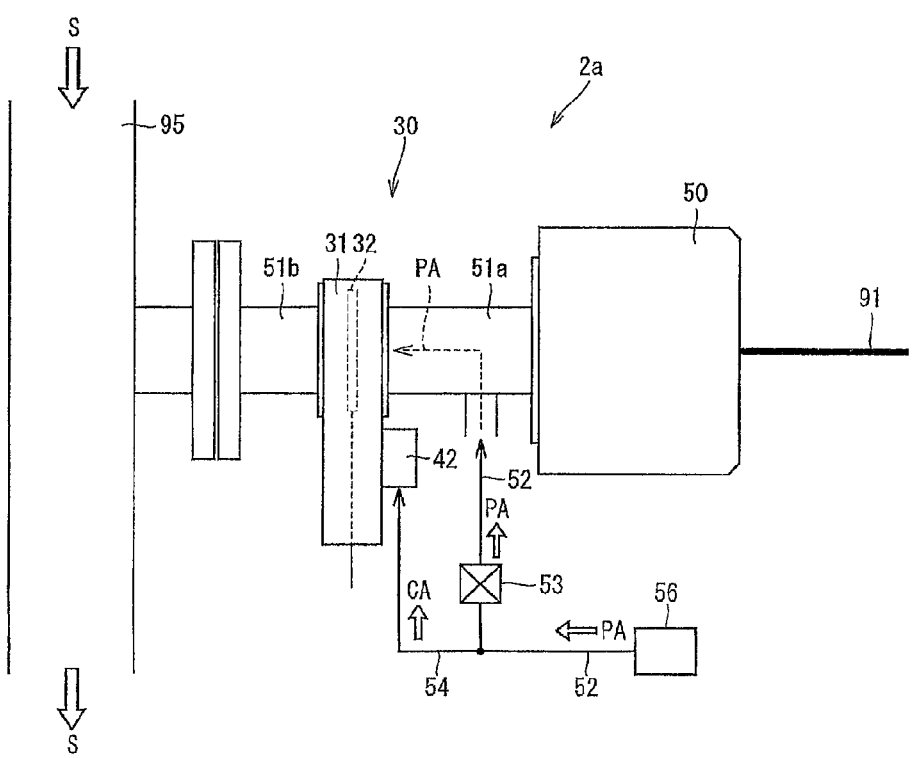
Figure 2:
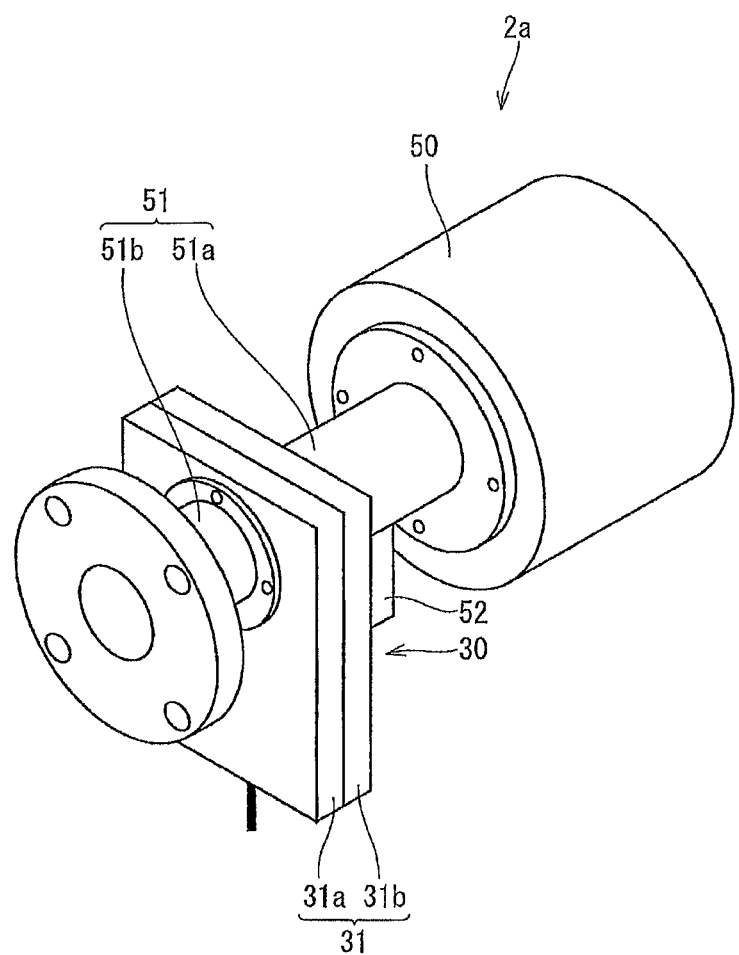
FIG. 2 is a perspective view of a light-emitting unit and its surroundings of the optical analyzer shown in FIG. 1A and FIG. 1B.

FIG. 1A and FIG. 1B are side views illustrating a light-emitting unit and its surroundings in an optical analyzer having an air-driven shutter device according to one embodiment. FIG. 2 is a perspective view of the same as that of FIG. 1A and FIG. 1B.

An analysis unit 2 (see FIG. 5) includes an analyzing unit 2a on the light-emitting side, and the analyzing unit 2a includes a light-emitting unit 50 to which one end of a first optical fiber 91 is fixed. A hollow light guiding tube 51 (a light guiding tube 51a, and a light guiding tube 51b) has one end connected to the light-emitting unit 50, through which laser light transmitted from the first optical fiber 91 passes. The other end of the light guiding tube 51 is connected to an opening formed on a side surface of a gas cell 95 (corresponding to the measurement field). It should be noted that on the other side surface of the gas cell 95, an analyzing unit 2b is disposed on the light-receiving side (see FIG. 5) opposing the analyzing unit 2a on the light-emitting side, and the analyzing unit 2b receives the laser light transmitted from the analyzing unit 2a.

A first pipe 52 is connected to a portion of the light guiding tube 51 near the light-emitting unit 50. The purge air PA supplied from a purge air supplying unit 56 is delivered through the first pipe 52 toward the light-emitting unit 50. Since the purge air PA is sent toward the light-emitting unit 50, dust is prevented from adhering to the light-emitting unit 50. In other words, the light-emitting unit 50 is always kept clean. In addition, the purge air PA results in a gas flow from the light guiding tube 51 toward the gas cell 95, such that the sample gas S flowing through the gas cell 95 is unlikely to flow into the light guiding tube 51. Accordingly, the contamination of the light-emitting unit 50 due to the contact with the sample gas S is prevented. The light-emitting unit 50 may or may not have an optically transparent window. If the light-emitting unit 50 has an optically transparent window, the purge air PA prevents the contamination of the optically transparent window.

Along the first pipe 52, a regulator 53 is provided for controlling the pressure of the purge air PA.

Along the light guiding tube 51 (i.e., between the light guiding tube 51a and the light guiding tube 51b), an air-driven shutter device 30 is provided. The air-driven shutter device 30 includes a cabinet 31, an opening 34 (see FIG. 3A) formed in the cabinet 31 and having a diameter similar to that of the light guiding tube 51, a shutter 32 movable in an up-and-down direction within the cabinet 31 and capable of closing or covering the opening 34, and a cylinder 42. A second pipe 54 branched from the first pipe 52 is connected to the cylinder 42. Pressure of air CA for opening and closing the shutter branched from the purge air PA is applied to the second pipe 54. In FIG. 1A, the purge air PA has a flow rate over a certain level, such that the air CA, which varies according to the purge air PA, has a pressure higher than a predetermined level. Accordingly, the pressure of the air CA pushes a piston 44 in the cylinder 42 (see FIG. 3B). Therefore, the shutter 32 is opened and fixed by the piston 44. The shutter 32 is provided with springs 39 (see FIG. 4). Although the springs 39 urge the shutter 32 in such a direction so as to close or cover the opening 34, when the pressure of the air CA is higher than the predetermined level, the piston 44 is fixed and not released. Accordingly, the shutter 32 does not move toward a closing direction (an upper direction in FIG. 1A)

FIG. 1B shows a state in which the purge air PA has a flow rate lower than the predetermined level. When the purge air PA has a flow rate lower than the predetermined level, the pressure of the air CA accordingly becomes lower than the predetermined level. As a result, the force for pushing the piston 44 weakens, so that the shutter 32 is released. Accordingly, the shutter 32 is pulled by the spring 39 and closes the opening 34.

As described above, in the air-driven shutter device 30, the air CA for opening and closing the shutter branched from the purge air PA is supplied as the power that controls the movement of the shutter 32. Accordingly, it is unnecessary to provide a dedicated power source (e.g., an electric power source) for driving the shutter 32 or for initiating the drive, and the configuration of a shutter device having a fail-safe function is simplified. The cost saving is also realized. In addition, since it is unnecessary to provide a dedicated power source for driving the shutter 32 or for initiating the drive, the shutter device can be installed easily.

Moreover, the pressure of the air CA for opening and closing the shutter is associated with the flow rate of the purge air PA. Therefore, when the pressure of the air CA becomes less than the predetermined level, the shutter 32 closes the opening 34, and it is possible to prevent the contamination of the light-emitting unit 50 caused by the contact with the sample S inflow due to a shortage of purge air PA. As a result, an optical analyzer 100 (see FIG. 5) can maintain high measurement accuracy. In addition, when the pressure of the air CA becomes less than the predetermined level, the shutter 32 closes the opening 34, and it is possible to prevent the sample gas from flowing toward the light-emitting unit 50 of the optical analyzer 100 due to the shortage of the purge air PA and to accordingly prevent the contact of the sample gas (e.g., hot gas or poisonous gas) with workers working around the light-emitting unit 50 during maintenance, for example. In other words, the workers are protected.

In addition, the shutter 32 is closed by the air CA, without an electric power. As a result, the device can be safely used in a place where explosion is likely to occur.

Furthermore, the gas stream from the light guiding tube 51 toward the gas cell 95, which is formed by the purge air PA, makes it difficult for dust to adhere to the shutter 32. As a result, it is possible to keep the friction between the driving parts of the shutter 32 sufficiently low.

Next, the structure of the air-driven shutter device 30 will be explained in detail.

Figure 4:
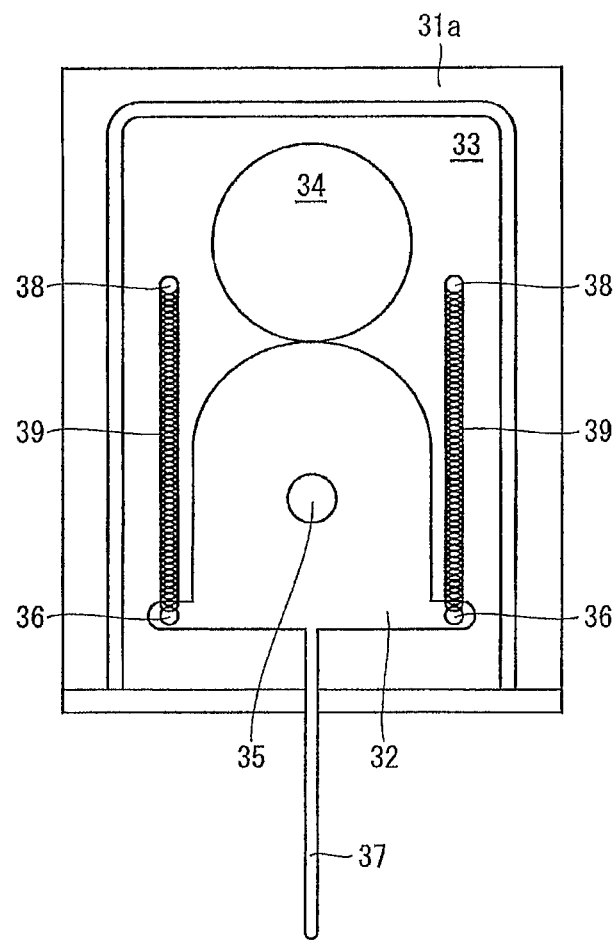
FIG. 4 is a rear cross-sectional view of the air-driven shutter device shown in FIG. 1A and FIG. 1B.

FIG. 3A is a front view of an air-driven shutter device shown in FIG. 1, FIG. 3B is a right side surface cross-sectional view of the device, FIG. 3C is a rear view of the device, and FIG. 3D is a bottom view of the device. FIG. 4 is a rear cross-sectional view of the air-driven shutter device shown in FIG. 1.

The air-driven shutter device 30 includes the cabinet 31. The cabinet 31 is composed of a plate-like body 31a having the opening 34 at the upper side in the center in a front view, and a plate-like body 31b fixed to the plate-like body 31a by means of screw. Between the plate-like body 31a and the plate-like body 31b, a space 33 is defined, in which the plate-like shutter 32 is disposed that is movable in the up and down direction.

The shutter 32 is provided, as shown in FIG. 4, with a concave engagement portion 35 in the center near the plate-like body 31b, and spring retaining portions 36 at two corners on the lower portion. A rod-like body 37 is connected to the lower portion of the shutter 32, so that the shutter 32 can be moved upward and downward by hand, for example.

In addition, at two corners on the upper side of the plate-like body 31a near the space 33 provided are spring retaining portions 38. The spring retaining portions 36 of the shutter 32 and the spring retaining portions 38 of the plate-like body 31a are connected to each other by means of the springs 39. The shutter 32 is positioned to cover the opening 34 through an elastic force of the springs 39, when external forces are not applied.

As shown in FIG. 3B, the plate-like body 31b is formed with a concave portion 41 below the opening 34 and having an opening 40 in the central portion. The cylinder 42 is provided to cover the concave portion 41. In a space defined between the concave portion 41 and the cylinder 42, the piston 44 is provided. The piston 44 includes a convex portion 43 that is fitted into the opening 40 and is longer than the depth of the opening 40.

The cylinder 42 is formed with a through hole 45 at the center, to which the second pipe 54 (see FIG. 1A) is connected. Accordingly, in response to the pressure of the air CA from the second pipe 54, the piston 44 is pushed toward the plate-like body 31a. While the pressure of the air CA is maintained at a level higher than the predetermined level, if the rod-like body 37 is pulled, for example, to impart stress to the spring 39, the concave engagement portion 35 of the shutter 32 is positioned so as to be aligned with the convex portion 43 of the piston 44. Then, due to the pressure of the air CA, the concave engagement portion 35 of the shutter 32 is engaged with the convex portion 43 of the piston 44 and the shutter 32 is accordingly fixed thereby.

In the above-described state, if the pressure of the air CA becomes lower than the predetermined level, the stress of a spring 46 provided in the piston 44 pushes the piston 44 back, and the convex portion 43 is released from the concave engagement portion 35, i.e., the convex portion 43 is disengaged with the concave engagement portion 35. As a result, the shutter 32 closes the opening 34.

As described above, in the air-driven shutter device 30, the pressure of the air CA for opening and closing the shutter is not used as a power for driving the shutter 32, but is used as a power for initiating the drive for the shutter 32 to close the opening, which does not require a high pressure. On the other hand, if springs 39 having a greater spring constant are employed and a higher stress is applied to the spring 39 for engagement, when the pressure of the air CA becomes lower than the predetermined level, the shutter 32 would be driven toward closing by a larger force. As a result, it is possible to prevent situations in which the shutter 32 cannot be closed due to adhesion of the shutter 32 to the cabinet 31 and an increase of frictional resistance caused by the dust. In other words, the fail-safe function is effectively fulfilled.

In addition, after the opening is closed, even if the pressure of the air CA becomes higher than the predetermined level again, the shutter 32 is kept closed by the stress of the springs 39. Therefore, in order to realize the opening state again, a worker has to manipulate the shutter, for example. In other words, in the air-driven shutter device 30 according to the present embodiment, the worker checks for causes resulting in a low flow rate of the purge air, and then the worker manipulates the rod-like body 37 to open the shutter 32. Accordingly, it is possible to check for every reason behind an error, and therefore serious troubles can be efficiently prevented.

In the above-described embodiment, the springs 39 (i.e., an elastic member which is made of a non-elastic member given elasticity through its form or processing) was used for explanation. However, an elastic body is not limited to springs. The elastic body may be a mechanism having elasticity such as a cylinder containing liquid, and a member made of materials having elasticity such as rubber. It should be noted, however, that the springs are preferable in light of simplification of the structure and reliability thereof.

The second pipe or the cylinder may be formed with an air-bleeding hole. In this case, if the flow rate of the purge air is higher than a certain level, the pressure of the air for opening and closing the shutter is maintained to be higher than the predetermined level. If the flow rate of the purge air becomes lower than the certain level, the pressure within the cylinder immediately decreases, and the engagement is immediately released. In other words, when the flow rate of the purge air becomes lower than the certain level, the shutter can be immediately closed.

Although the stress of the spring 39 is used for closing the shutter 32 in the above-described embodiment, the shutter may be closed by its own weight. As an example, the springs 39 may be removed from the air-driven shutter device 30 shown in FIG. 1, and the device can be installed upside down. As another example, a configuration can be employed wherein the pressure of the air for opening and closing the shutter directly moves the shutter up for opening, and when the pressure of the air becomes lower than the predetermined level, the shutter moves down for closing due to its own weight.

1-2. Optical Analyzer

Next, a case will be explained in which the air-driven shutter device 30 is employed in an optical analyzer.

Figure 5:
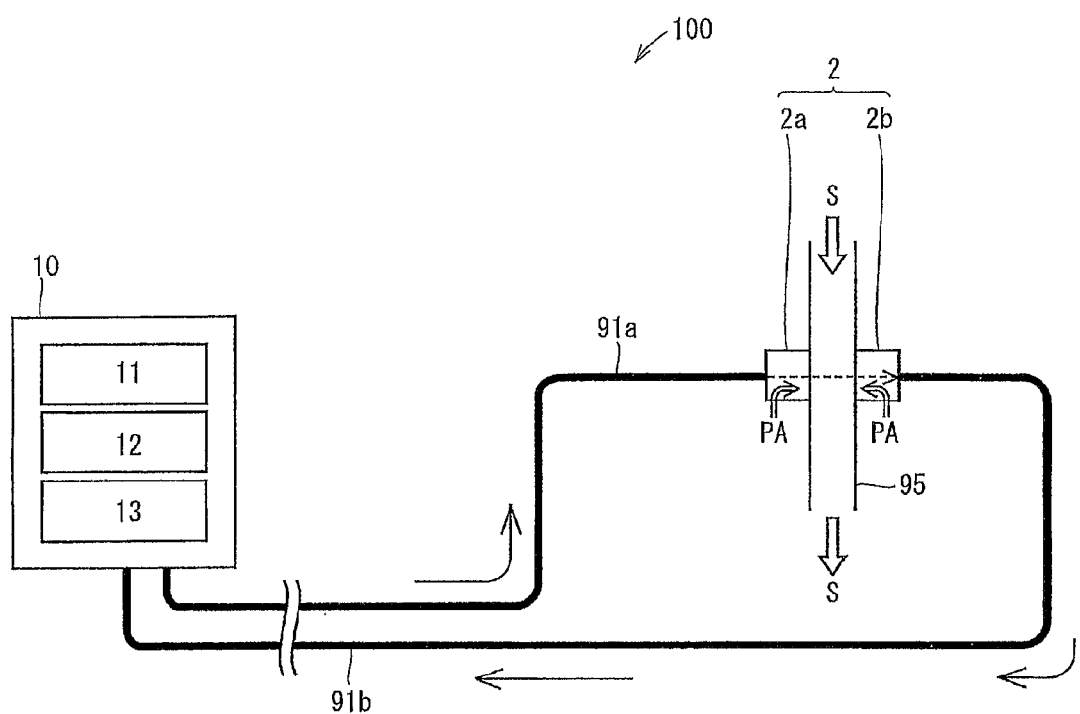
FIG. 5 is a block diagram illustrating the optical analyzer including the air-driven shutter device shown in FIG. 1A and FIG. 1B.

FIG. 5 is a block diagram illustrating the structure of an optical analyzer including an air-driven shutter device shown in FIG. 1. The optical analyzer 100 according to the present embodiment includes a measuring device 10, an analysis unit 2, and an optical fiber 91 (an optical fiber 91a and an optical fiber 91b) for optically connecting the measuring device 10 and the analysis unit 2.

The measuring device 10 is a typical measuring unit including a light source 11 (e.g., laser or LED) emitting a measuring light, a light detecting unit 12 (e.g., a photodiode), and a control device 13. The control device 13 controls the operation of the light source 11 and the light detecting unit 12. The control device 13 calculates density of the object to be analyzed based on signals received by the light detecting unit 12. The control device 13 may be composed of analog circuits or digital circuits such as a CPU.

The measuring device 10 only has to measure objects using light, and is not limited to one type. An absorption spectrochemical method such as TDLAS (Tunable Diode Laser Absorption Spectroscopy) is one example. When using TDLAS, the measuring device 10 can perform a gas concentration measurement of $O_2$, $CO$, $CO_2$, $H_2O$, $NH_3$, $HCl$, etc., having absorption spectrum between infrared region and near-infrared region based on a selection of measuring absorption waves. In addition, the measuring device 10 can perform a gas concentration measurement of $SO_2NO$, $NO_2$, etc., having absorption spectrum in the mid-infrared region, using a QCL (quantum-cascade laser) as a light source. It is also possible to measure the dust amount by applying a light in the visible light region and measure the transmitted amount of the light.

The optical fiber 91a and the optical fiber 91b are connected to the measuring device 10, and the light emitted from the measuring device 10 is, through the optical fiber 91a, guided into the analyzing unit 2a on the light-emitting side of the analysis unit 2. On the other hand, the light received by the analyzing unit 2b on the light-receiving side of the analysis unit 2 is, through the optical fiber 91b, input to the measuring device 10.

The analysis unit 2 includes the analyzing unit 2a on the light-emitting side and the analyzing unit 2b on the light-receiving side, and the analyzing unit 2a is provided on a side surface of the gas cell 95 and the analyzing unit 2b is provided on the other side surface. The analyzing unit 2a is connected to the optical fiber 91a, and can guide the light emitted from the light source 11 of the measuring device 10 into the gas cell 95. The light guided from the analyzing unit 2a into the gas cell 95 is attenuated due to the objects (e.g., $O_2$, CO, $CO_2$, $H_2O$, $NH_3$, HCl) to be analyzed in the sample gas S, and then is output to the analyzing unit 2b. The gas cell 95 corresponds to a measurement cell according to the present disclosure.

Since the analyzing unit 2a has been already explained with reference to FIG. 1 and FIG. 2, a detailed explanation will be omitted. The analyzing unit 2a includes the light-emitting unit 50 and the air-driven shutter device 30, and when the flow rate of the purge air PA emitted toward the light-emitting unit 50 becomes lower than a certain level, the shutter 32 is closed for blocking the light-emitting unit 50 from the sample gas S. The analyzing unit 2b has a similar structure to the analyzing unit 2a, with the only difference being that a light-receptive unit (not shown) is provided instead of the light-emitting unit 50.

The purge air PA is branched into another pipe (not shown) different from the second pipe 54, and is supplied to the air-driven shutter device 30 of the analyzing unit 2b. If the flow rate of the purge air PA becomes lower than a predetermined threshold or level, the air-driven shutter device 30 of the analyzing unit 2a is closed, and the air-driven shutter device 30 of the analyzing unit 2b is closed. In the present embodiment, a case will be explained in which the air-driven shutter device 30 is provided in both of the analyzing unit 2a and the analyzing unit 2b. However, the air-driven shutter device 30 may also be provided in only one of them. However, it is preferable for some applications that the air-driven shutter device is provided in both of the analyzing unit on the light-emitting side and the analyzing unit on the light-receiving side.

According to the optical analyzer 100, the light source and the light-emitting unit 50 are connected through the optical fiber 91, and the light-receptive unit and the light detecting unit are connected through the optical fiber 91. The entire optical path is also composed of optical fibers. Accordingly, the flexibility of the arrangement is improved, and the analysis unit 2 can be freely positioned. For example, a length of the optical fiber 91 is set to be about 1000 m to locate the analysis unit 2 away from the measuring device 10, so that objects that are highly explosive can be safely measured. In addition, it becomes extremely easy to install the analysis unit 2 in a chamber while installing the measuring device 10 out of the chamber for in-situ measurement.

Although the analysis unit 2 includes both the analyzing unit 2a on the light-emitting side and the analyzing unit 2b on the light-receiving side in the above-described embodiment, the present invention is not limited to this embodiment. For example, instead of the analyzing unit 2b on the light-receiving side, a reflecting mirror MR may be provided to reflect the light emitted from the light source toward the optical fiber 91 (the analyzing unit 2a on the light-emitting side). In this case, it is preferable that the air-driven shutter device is provided between the reflecting mirror MR and the gas cell.

2. Second Embodiment

Figure 6:
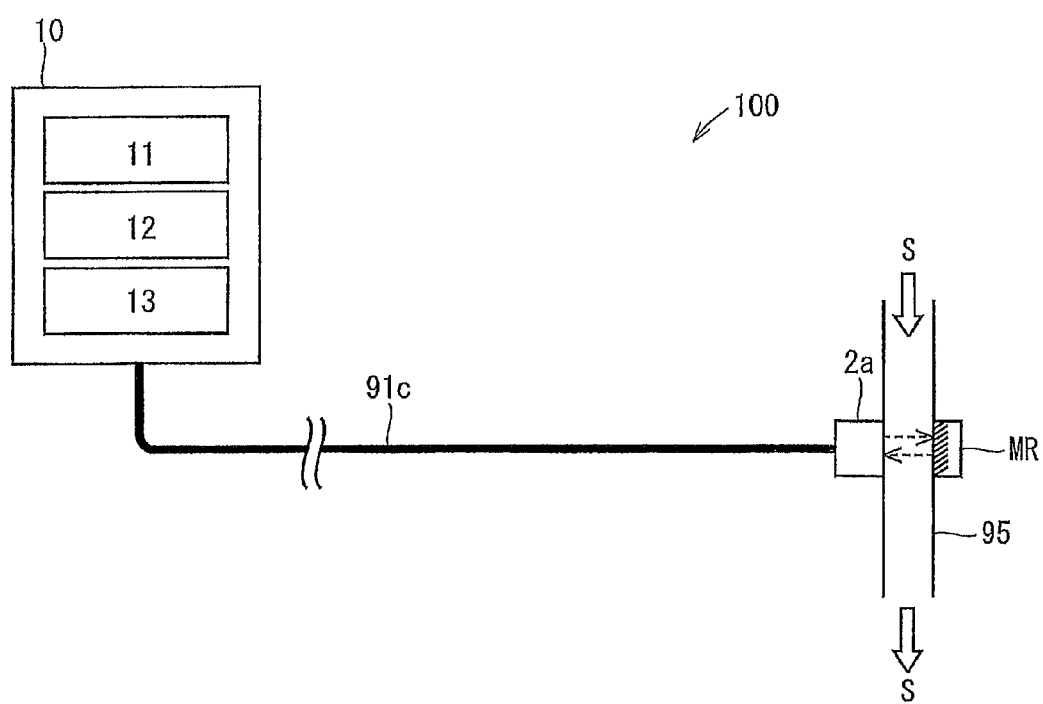
FIG. 6 is a partial schematic diagram of the optical analyzer according to another embodiment.

FIG. 6 is a partial schematic diagram showing an optical analyzer according to another embodiment.

If a reflecting mirror MR is arranged instead of the analyzing unit 2b on the light-receiving side, the measuring device 10 and the analyzing unit 2a on the light-emitting side are connected with each other through a fiber 91c. Accordingly, the light transmitted from the analyzing unit 2a on the light-emitting side and returns after passing through the gas cell 95 is guided again into the fiber 91c, and the light intensity of the reflected light is measured by the light detecting unit 12.

In the optical analyzer according to the present embodiment in addition to the optical analyzer 100 explained with reference to FIG. 1 through FIG. 6, an air valve may be provided upstream of a branch between the first pipe 52 and the second pipe 54. The air valve switches the flow path from the purge air supplying unit 56 to outside air if the pressure of the purge air PA becomes lower than the predetermined level. This configuration functions effectively, especially when the pressure of sample gas is lower than the atmospheric pressure and the atmospheric pressure is higher than the pressure of the purge air in a normal state. This example will be explained hereinafter.

Figure 7A:
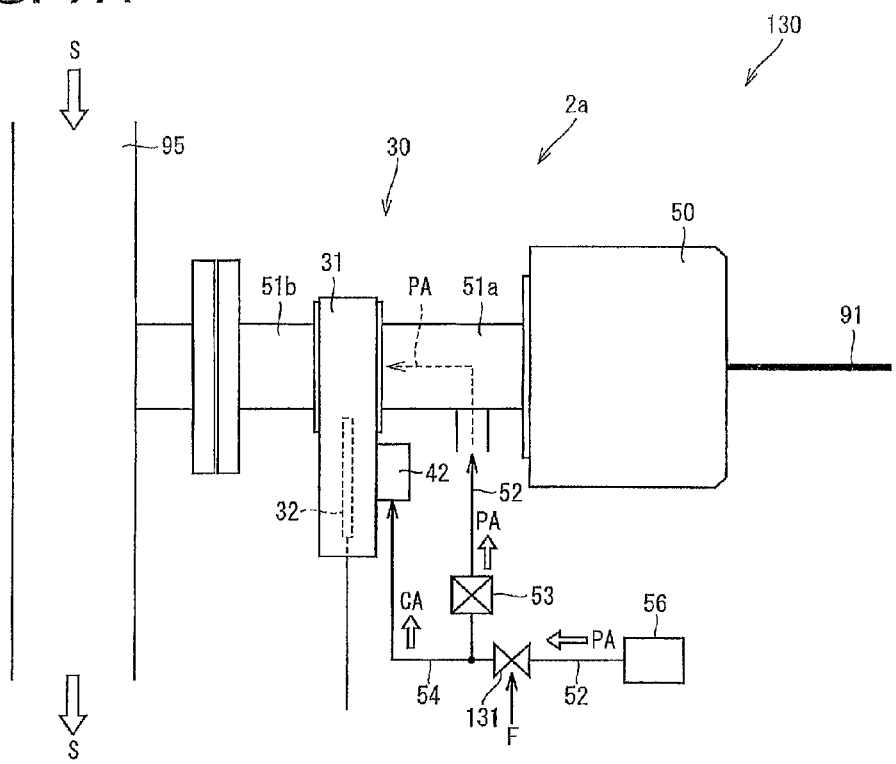
FIG. 7A is a side view illustrating the light-emitting unit and its surroundings of the optical analyzer according to another embodiment.

FIG. 7A is a side view illustrating a light-emitting unit and its surroundings in the optical analyzer according to another embodiment. As shown in FIG. 7A, an optical analyzer 130 is provided with an air valve 131 upstream of a branch between the first pipe 52 and the second pipe 54. If the pressure of the purge air PA becomes lower than the predetermined level, the air valve 131 switches the flow path from the purge air supplying unit 56 to outside air F. The air valve 131 may be a well-known one. It should be noted that other components of the optical analyzer 130 are similar to those of the optical analyzer 100 explained with reference to FIG. 1 through FIG. 6, so the explanation is omitted.

Figure 7B:
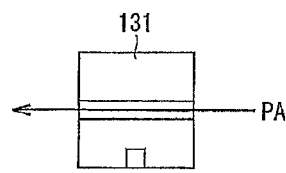
FIG. 7B and FIG. 7C are views showing the movement of the air valve.

Hereinafter, a case will be explained in which the pressure of the sample gas S is lower than the atmospheric pressure and the atmospheric pressure is higher than the pressure of purge air PA in a normal state. If the pressure of the purge air PA is normal, i.e., the pressure of the purge air PA is higher than the predetermined level, the flow path of the air valve 131 allows the purge air PA from the purge air supplying unit 56 to pass therethrough (see FIG. 7B).

Figure 7C:
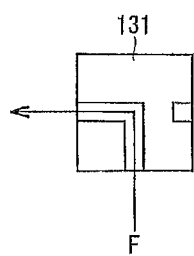

If the pressure of the purge air PA becomes lower than the predetermined level, the flow path of the air valve 131 shuts off the flow path from the purge air supplying unit 56, thereby allowing the outside air F to pass through (see FIG. 7C). Since the pressure of the sample gas S is lower than the atmospheric pressure, the outside air F, in place of the purge air PA from the purge air supplying unit 56, flows into the first pipe 52 and the second pipe 54. The outside air F flowing in the first pipe 52 flows through the light guiding tube 51 toward the gas cell 95, so that it is possible to reduce or prevent the dust from being adhered to the light-emitting unit 50, i.e., always keeping the light-emitting unit 50 clean. It should be noted that since the pressure of the outside air F flowing in the second pipe 54 is higher than the pressure of the purge air PA in a normal state, the shutter 32 is not closed.

Next, a case will be explained in which the pressure of the sample gas S increases and as a result (the pressure of the outside air F)−(the pressure of the sample gas S) becomes lower than the predetermined level when the flow path of the air valve 131 allows the outside air F to pass (see FIG. 7C). This explanation is based on an assumption that pressure of the sample gas S suddenly increases, for example. In this case, the pressure in the cylinder 42 becomes lower than the predetermined level, and then the shutter 32 is closed.

As described above, since the optical analyzer 130 is provided with the air valve 131, even if the supply of the purge air PA is stopped or reduced from the purge air supplying unit 56 for some reason, the shutter 32 is not closed. As a result, the measurement can be continued. In addition, only when the pressure of the sample gas S increases abruptly, the shutter 32 is closed to prevent the contamination of the light-emitting unit 50 due to contact of the sample gas S. Although the optical analyzer was provided with the air-driven shutter device 30 in the previous example explained with reference to FIG. 7, only if the flow path of the air valve become a state of FIG. 7C when the pressure of the purge air becomes lower than the predetermined level, sufficient effects can be achieved without an air-driven shutter device.

3. Third Embodiment

The air-driven shutter device may also employ the following structure.

Figure 8:
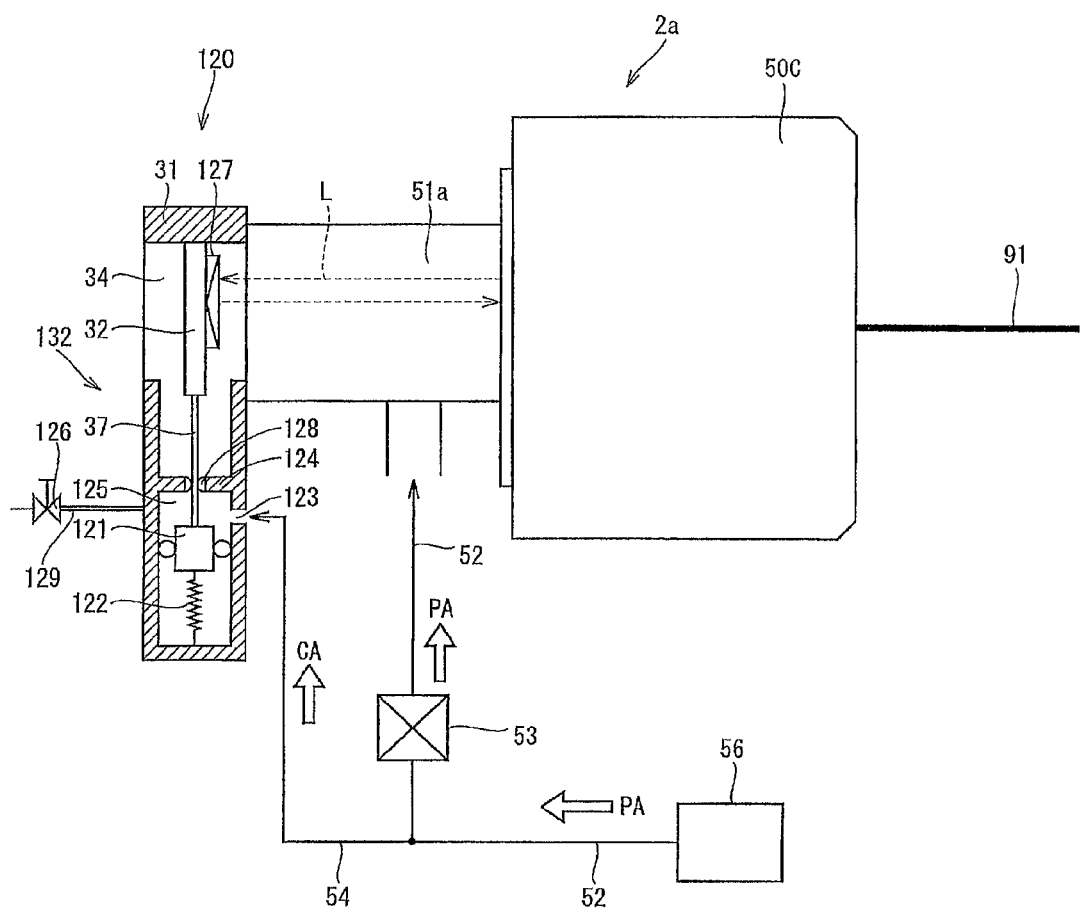
FIG. 8 is a side view of the light-emitting unit of the optical analyzer and its surroundings, including the air-driven shutter device according to another embodiment.

FIG. 8 is a side view illustrating a light-emitting unit and its surroundings in an optical analyzer including an air-driven shutter device according to another embodiment. For ease of explanation, the air-driven shutter device is illustrated with a partial cross-sectional view.

An air-driven shutter device 120 shown in FIG. 8 includes a cabinet 31, an opening 34, a shutter 32, a rod-like body 37, a moving part 121, and a spring 122. The opening 34 is formed in the cabinet 31, and has a diameter the same as or nearly equal to that of the light guiding tube 51a. The shutter 32 can move within the cabinet 31 in an up-and-down direction, and can close the opening 34. The rod-like body 37 is disposed under the shutter 32. The moving part 121 is provided at the other end of the rod-like body 37, and can slide within the cabinet 31. The spring 122 is disposed between the other end of the moving part 121 and the lower end within the cabinet 31. A shutter opening and closing mechanism 132 is a mechanism for opening and closing the shutter 32 and maintaining the open and closed states. The shutter opening and closing mechanism 132 includes the spring 122 and a space 125 (to be described later).

The cabinet 31 is formed with a through hole 123 on a side surface thereof. A second pipe 54 branched off from the first pipe 52 is connected to the through hole 123. The through hole 123 is connected to a space 125 defined between an upper wall 124, which is disposed in the cabinet 31 near the center, and the moving part 121. The space 125 is pressurized with the air CA from the second pipe 54. Then, if the pressure of the air CA becomes higher than the predetermined level, the moving part 121 moves downward, and the shutter 32 is opened accordingly. On the other hand, along the pipe 129 in communication with the space 125 of the cabinet 31, a needle valve 126 is provided. Through the needle valve 126, the air CA is released outside from the space 125 at a constant rate. During normal measurement, while the air CA is released outside from the needle valve 126, the space 125 is sufficiently pressurized because the air CA is sufficiently supplied through the through hole 123. In contrast, if the gas supplied from the purge air supplying unit 56 is decreased or stopped, and the pressure of the air CA in the space 125 becomes lower than the predetermined level, the moving part 121 is urged upward due to elasticity of the spring 122, and the shutter 32 is closed. In the upper wall 124, a sealing material 128 is provided to be in contact with the rod-like body 37 so as to ensure air tightness of the space 125.

The shutter 32 is provided with a mirror 127 near the light emitting and receiving unit 50c. The mirror 127 reflects measuring light L emitted from the light emitting and receiving unit 50c back toward the light emitting and receiving unit 50c when the shutter 32 is closed. A span gas from a pipe (not shown) may fill the light guiding tube 51a to calibrate the measuring light L when the shutter 32 is closed. As described above, according to the air-driven shutter device 120, first of all, the pressure of the gas (the pressure of the air CA for opening and closing the shutter) from the purge air supplying unit 56 is decreased to a level lower than the predetermined level so as to close the shutter 32, in order to stop the sample from flowing into the light guiding tube 51a. Then, the measuring light L is calibrated without any sample in the light guiding tube 51a. After the calibration, the pressure of the gas supplied from the purge air supplying unit 56 is increased again to a level higher than the predetermined level to open the shutter 32 and measure the sample. Accordingly, the air-driven shutter device 120 facilitates the automatic calibration of the measuring light without having any worker visit the site.

Although the measurement field was the gas cell 95 in the above-described embodiments, the present disclosure is not limited to such an arrangement. For example, the measurement field may be within a tubular probe for gas analysis disposed perpendicular to the flow of the sample in a pipe and through which the measuring light passes. Hereinafter, an embodiment will be explained in which the optical analyzer employs the probe for gas analysis.

4. Fourth Embodiment

Figure 9:
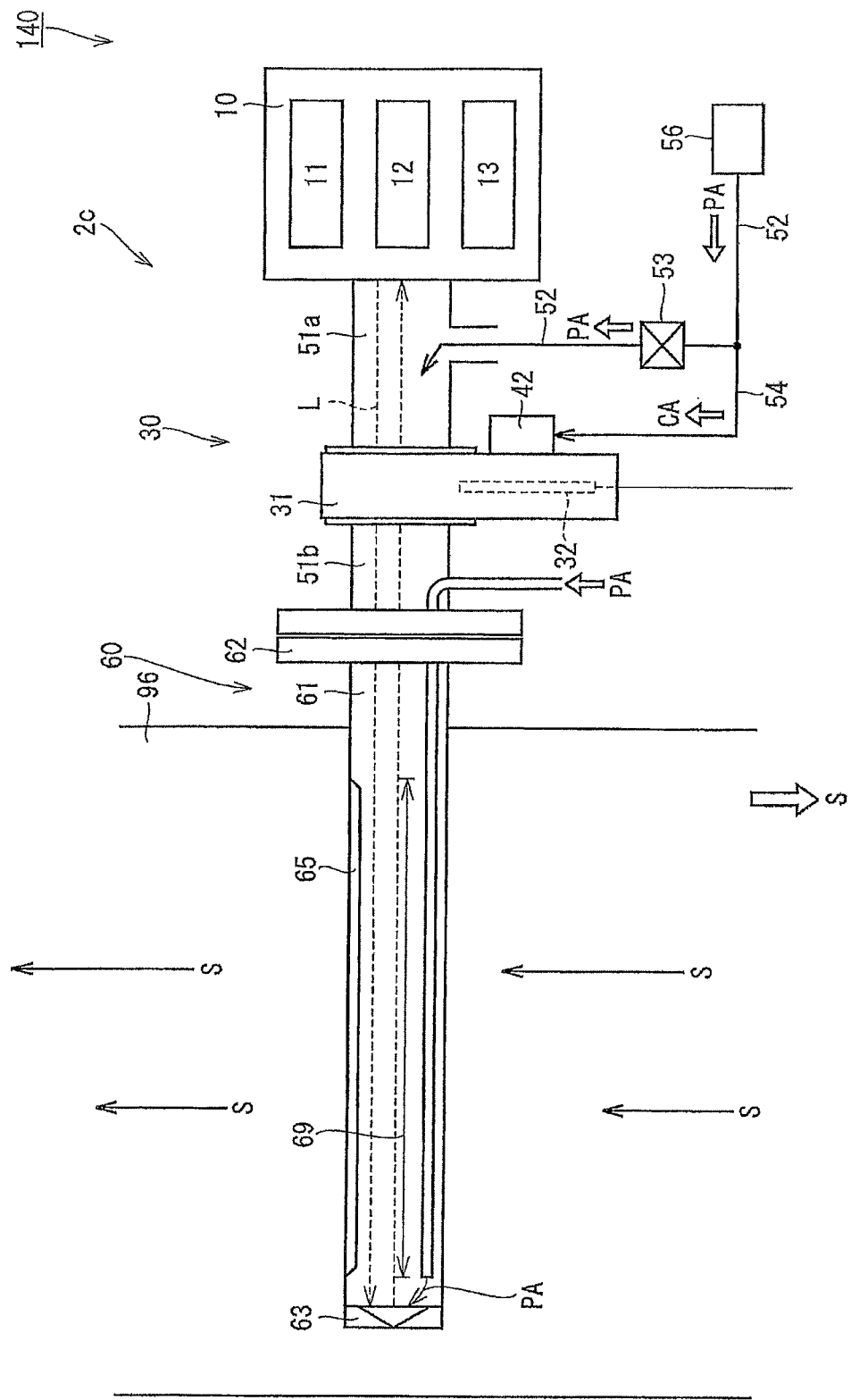
FIG. 9 is a schematic diagram of an optical analyzer according to another embodiment.

FIG. 9 is a schematic diagram of an optical analyzer according to another embodiment.

An optical analyzer 140 according to the present embodiment includes a measuring device 10 and an analysis unit 2c. The measuring device 10 has already been explained previously, so the explanation is omitted here.

The analysis unit 2c includes a probe for gas analysis 60, a hollow light guiding tube 51 (51a, 51b) for guiding laser light L emitted from the light source 11 toward the probe 60, and an air-driven shutter device 30 disposed in the middle of the light guiding tube 51. The probe for gas analysis 60 includes a tubular member 61 and a flange 62 disposed at one end of the tubular member 61. The tubular member 61 and the light guiding tube 51b are connected with each other via the flange 62. The air-driven shutter device 30 has already been explained previously, so the explanation is omitted here.

The tubular member 61 is disposed in a pipe 96 through which the sample gas S flows, and is arranged to be perpendicular to the flow of the sample gas S. The tubular member 61 is formed with a plurality of openings 65 only on its downstream side with respect to a flow direction of the sample gas S, and the openings 65 are formed along an entire length of a measurement field 69 in the tubular member 61. The openings 65 enable the sampling of the sample gas S. Although the tubular member 61 is disposed in the pipe 96 through which the sample gas S flows and is arranged generally perpendicular to the flow of the sample gas S in the present embodiment, the present disclosure is not limited to this example. The tubular member only has to be disposed in the pipe through which the sample gas flows to cross the flow of the sample gas. For example, the tubular member can be obliquely disposed such that one end of the tubular member opposite the flange is positioned downstream of the flange.

The tubular member 61 is formed with the openings 65 on its downstream side with respect to the flow direction of the sample gas S to receive the sample gas. The tubular member 61 is not formed with openings on its upstream side for receiving the sample gas S. Accordingly, the dust mixed in the sample gas S does not enter the tubular member 61 from the upstream side. Since the tubular member 61 is formed with the openings only on the downstream side, along the entire length of the measurement field 69, the sample gas S flows around the tubular member 61 and flows into the tubular member 61 through the openings 65. In contrast, the dust mixed in the sample gas S continues to move in the direction of movement (downstream direction) under the law of inertia because the dust has a certain degree of mass. Accordingly, the dust does not tend to flow around the tubular member 61 and through the openings 65. It should be noted that the downstream side includes positions up to a maximum of about 60 degrees in each direction from the most downstream point of the tubular member 61 when the tubular member 61 is seen in the longitudinal direction and divided along a circumferential direction. The angle is preferably less than about 45 degrees.

A mirror 63 is disposed at the other end of the tubular member 61 to reflect the laser light emitted from the light source 11 toward the light detecting unit 12. Accordingly, the light detecting unit 12 measures the light intensity of the reflected light, and the objects in the sample gas S can be measured based on the attenuation amount of the light.

The probe for gas analysis may be provided with a cover for opening and closing the openings 65. Hereinafter, this example will be explained with reference to FIG. 10 and FIG. 11.

FIG. 10A and FIG. 10B are longitudinal sectional views of a probe for gas analysis according to another embodiment. A probe for gas analysis 74 shown in FIG. 10A and FIG. 10B is provided with a tubular member 76 that is in contact with the tubular member 61 of the probe 60 shown in FIG. 9 from the inside. The tubular member 76 is formed with openings 75 along one entire surface. The tubular member 76 corresponds to the above-described cover. In the optical analyzer including the probe 74, as shown in FIG. 10A, when the openings 75 of the tubular member 76 and the openings 65 of the tubular member 61 have a positional relationship in which there is communication in between, the sample gas S can be analyzed in a same way as in the above-described optical analyzer 140.

If the tubular member 76 is turned from the state of FIG. 10A, the openings 75 of the tubular member 76 and the openings 65 of the tubular member 61 have a positional relationship in which there is no communication in between, as shown in FIG. 10B. In this state, the sample gas S cannot flow into the tubular member 61. Accordingly, in this state, the tubular member 61 may be filled with a span gas to calibrate the measuring light. As described above, according to the probe 74, the tubular member 61 can be used for calibration as well as measurement, thereby simplifying the configuration of the probe for gas analysis. In addition, when the tubular member 76 is turned, the edges of the openings 75 of the tubular member 76 remove the dust adhered to the inner wall of the tubular member 61. The tubular member 76 may be turned by hand or by electrical power.

FIG. 11A and FIG. 11B are transverse sectional views of a probe for gas analysis according to another embodiment. In a probe for gas analysis 78 shown in FIG. 11A and FIG. 11B, the tubular member 61 is formed with ribs 79 and openings 80 having the substantially same width. A tubular member 82 is disposed within the tubular member 61 such that the tubular member 82 is in contact with the tubular member 61 from the inside. The tubular member 82 is formed with a plurality of apertures 81 having the substantially same width as that of the openings 80. The apertures 81 are formed near the ribs 79 and the openings 80 of the tubular member 61. The tubular member 82 corresponds to the above-described cover. In the optical analyzer having the probe 78, when the apertures 81 of the tubular member 82 and the openings 80 of the tubular member 61 have a positional relationship in which there is communication in between, as shown in FIG. 11A, it is possible to analyze the sample gas S in a same way as in the above-described optical analyzer 140.

When the tubular member 82 slides in a longitudinal direction (right and left direction in FIG. 11) from a state of FIG. 11A, the apertures 81 of the tubular member 82 and the openings 80 of the tubular member 61 have a positional relationship in which there is no communication in between, as shown in FIG. 11B. In this state, the sample gas S can not flow into the tubular member 61. Accordingly, in this state, the tubular member 61 may be filled with a span gas to calibrate the measuring light. As described above, according to the probe 78, the tubular member 61 can be used for calibration as well as measurement, thereby simplifying the configuration of the probe for gas analysis. In addition, when the tubular member 82 slides in the longitudinal direction, the edges of the apertures 81 of the tubular member 82 remove the dust adhered to the inner wall of the tubular member 61. The tubular member 82 can be slid by hand or by electrical power.

Although, the sample in the above-described embodiment was gas (sample gas S), the present disclosure is not limited to this example. The sample may also be liquid.

In the above-described embodiment, density of the gas was being analyzed. However, it is acceptable that the optical analyzer according to the present disclosure is a thermometer based on TDLAS (Tunable Diode Laser Absorption Spectroscopy). If a similar structure of the optical analyzer 100 is employed, a dust measurement device may also be employed as an embodiment that measures dust density by measuring the transmittance attenuation of the measuring light caused by the dust.

While only selected embodiments have been chosen to describe the present invention, it will be apparent to those skilled in the art from this disclosure that various changes and modifications can be made herein without departing from the scope of the invention defined in the appended claims. Furthermore, the foregoing descriptions of the embodiments according to the present invention are provided as examples only, and are not meant to limit the invention defined by the appended claims and their equivalents. Thus, the scope of the invention is not limited to the disclosed embodiments. While various embodiments may have been described as providing advantages or being preferred over other embodiments with respect to one or more desired characteristics, as one skilled in the art is aware, one or more characteristics may be compromised to achieve desired system attributes, which depend on the specific application and implementation. These attributes include, but are not limited to: cost, strength, durability, life cycle cost, marketability, appearance, packaging, size, serviceability, weight, manufacturability, ease of assembly, etc. Any embodiments described as less desirable than other embodiments or prior art implementations with respect to one or more characteristics are not outside the scope of the disclosure and may be desirable for particular applications. While the best mode has been described in detail, those familiar with the art will recognize various alternative designs and embodiments within the scope of the following claims.

What is claimed is:

1. An air-driven shutter device for an optical analyzer, the optical analyzer including a measurement field to which a sample gas is supplied, a light-emitting unit configured to emit measuring light to the sample gas in the measurement field, a light-receptive unit configured to receive the measuring light that has passed through the sample gas, and a purge air supplying unit configured to supply a purge air, the air-driven shutter device comprising:

a shutter provided between the measurement field and at least one of the light-emitting unit and the light-receptive unit, the shutter in a closed position being configured to block a flow of the sample gas in the measurement field toward the at least one of the light-emitting unit and the light-receptive unit; and a shutter opening and closing mechanism configured to open the shutter while a pressure of a gas supplied from the purge air supplying unit is higher than a predetermined level, and to close the shutter when the pressure of the gas supplied from the purge air supplying unit becomes lower than a predetermined level.

2. The air-driven shutter device according to claim 1, wherein the shutter opening and closing mechanism includes an elastic body, and the shutter is configured to be kept open through an engagement while a force is applied to the elastic body, and the shutter opening and closing mechanism is configured to release the engagement in order to close the shutter by an elastic force of the elastic body when the pressure of the gas supplied from the purge air supplying unit becomes lower than the predetermined level.

3. The air-driven shutter device according to claim 1, wherein the shutter opening and closing mechanism includes a space, to which gas is supplied from the purge air supplying unit, and an elastic body, and the shutter opening and closing mechanism controls the opening and closing of the shutter based on the pressure of the gas supplied into the space and an elastic force of the elastic body.

4. The air-driven shutter device according to claim 1, wherein the shutter opening and closing mechanism includes:

an elastic body disposed to urge the shutter toward closing;

a cylinder disposed to fix the shutter in an open state with the pressure of the gas supplied from the purge air supplying unit, and to release the shutter when the pressure of the gas becomes lower than the predetermined level.

5. The air-driven shutter device according to claim 4, wherein:

the shutter opening and closing mechanism includes a cabinet, the cabinet including a first plate-like body and a second plate-like body, with a space disposed in between, the first plate-like body including an opening to be closed by the shutter, and the second plate-like body is formed with a concave portion and a second opening in the concave portion, the shutter is disposed to move up and down in the space, the cylinder is arranged to cover the concave portion, and the shutter opening and closing mechanism further includes a piston in a space defined between the concave portion and the cylinder, the piston having a convex portion with a length longer than a depth of the second opening, the convex portion is arranged to fit into the second opening.

6. The air-driven shutter device according to claim 5, wherein the shutter is formed with an engagement portion, a space is defined between the concave portion and the cylinder, into which the gas is supplied from the purge air supplying unit, and the piston is disposed such that the convex portion is engaged with the engagement portion of the shutter with the pressure of the gas.

7. The air-driven shutter device according to claim 1, wherein the shutter opening and closing mechanism includes:

a cabinet having a space in which the shutter is disposed, the cabinet being formed with an opening;

a moving part connected to the shutter and movable within the cabinet; and an elastic body configured to urge the moving part so that the shutter closes the opening.

8. An optical analyzer comprising:

a measurement field to which a sample is supplied;

a light-emitting unit configured to emit measuring light to the sample in the measurement field;

a light-receptive unit configured to receive the measuring light that has passed through the sample;

a purge air supplying unit configured to supply a purge air;

a first pipe configured to guide a gas supplied from the purge air supplying unit toward at least one of the light-emitting unit and the light-receptive unit;

a second pipe branched off from the first pipe such that the pressure of the gas in the second pipe varies according to the flow rate of the purge air; and an air-driven shutter device according to claim 1, being connected to the second pipe.

9. The optical analyzer according to claim 8, further comprising a tubular probe for gas analysis that is disposed in a pipe through which the sample flows such that the probe crosses the flow of the sample, and through which the measuring light passes, wherein the measurement field is provided within the probe, the probe is formed with an opening for receiving the sample, and further comprising a cover configured to open and close the opening.

10. A method of operating an optical analyzer including a measurement field to which a sample gas is supplied, a light-emitting unit configured to emit measuring light to the sample gas in the measurement field, and a light-receptive unit configured to receive the measuring light that has passed through the sample gas, the method comprising:

opening a shutter disposed between the measurement field and at least one of the light-emitting unit and the light-receptive unit using gas pressure, from a purge gas unit; and closing the shutter when the gas pressure becomes lower than an associated threshold to block a flow of the sample gas in the measurement field toward at least one of the light-emitting unit and the light-receptive unit.

11. The air driven shutter device according to claim 1, wherein the purge air supplying unit is configured to supply the purge air from the at least one of the light-emitting unit and the light-receptive unit toward the sample gas flowing into the measurement field.

* * * * *